(12) United States Patent  (10) Patent No.: US 8,507,852 B2
Makarov  (45) Date of Patent: Aug. 13, 2013

(54) APPARATUS AND METHODS FOR ION MOBILITY SPECTROMETRY

(75) Inventor: Alexander A. Makarov, Bremen (DE)

(73) Assignee: Thermo Fisher Scientific (Bremen) GmbH, Bremen (DE)

(*) Notice: Subject to any disclaimer, the term of this patent is extended or adjusted under 35 U.S.C. 154(b) by 56 days.

(21) Appl. No.: 13/327,396

(22) Filed: Dec. 15, 2011

(65) Prior Publication Data

US 2012/0153140 A1  Jun. 21, 2012

(30) Foreign Application Priority Data

Dec. 16, 2010 (GB) .................................. 1021360.1

(51) Int. Cl.
*H01J 49/36* (2006.01)
*H01J 49/26* (2006.01)
*H01J 49/00* (2006.01)

(52) U.S. Cl.
USPC ............ 250/290; 250/293; 250/281; 250/282

(58) Field of Classification Search
USPC .................. 250/281, 282, 286, 288, 290, 293
See application file for complete search history.

(56) References Cited

U.S. PATENT DOCUMENTS

| | | | | |
|---|---|---|---|---|
| 6,100,521 A * | 8/2000 | Doring et al. | ................ | 250/286 |
| 7,705,296 B2 * | 4/2010 | Wu | ............... | 250/282 |
| 7,838,821 B2 * | 11/2010 | Clemmer et al. | ............ | 250/281 |
| 8,258,468 B2 * | 9/2012 | Wu | ............... | 250/288 |
| 8,288,714 B2 * | 10/2012 | Makarov et al. | ............ | 250/283 |
| 2003/0150985 A1 * | 8/2003 | Guevremont et al. | ........ | 250/287 |
| 2003/0230711 A1 | 12/2003 | Guevremont et al. | | |
| 2005/0194532 A1 | 9/2005 | Guevremont et al. | | |
| 2006/0049363 A1 | 3/2006 | Guevremont | | |
| 2009/0189070 A1 * | 7/2009 | Clemmer et al. | ............ | 250/282 |
| 2011/0121171 A1 * | 5/2011 | Clemmer et al. | ............ | 250/282 |
| 2012/0091332 A1 * | 4/2012 | Makarov et al. | ............ | 250/282 |
| 2012/0138785 A1 * | 6/2012 | Makarov et al. | ............ | 250/282 |

FOREIGN PATENT DOCUMENTS

| | | |
|---|---|---|
| DE | 197 30 896 A1 | 1/1999 |
| GB | 2 327 531 B | 1/1999 |
| GB | 2 457 556 A | 8/2009 |
| GB | 2489310 A | 9/2012 |
| WO | WO 2006/056049 A1 | 6/2006 |
| WO | WO 2012/038268 A1 | 3/2012 |

* cited by examiner

*Primary Examiner* — Bernard E Souw
(74) *Attorney, Agent, or Firm* — Charles B. Katz

(57) ABSTRACT

There is provided of an on mobility spectrometer for separating ions according to their on mobility comprising, in various aspects: a drift tube having therein a drift space and in the drift space at least two on separation paths of different lengths: a straight drift tube having therein a helical ion separation path; a helical on separation path surrounding an axially extending inner electrode assembly; and a drift tube for separating ions according to their ion mobility wherein a rotating arcuate electric field is applied in operation to separate ions having an ion mobility such that their rotational velocity in the drift tube is matched to the rotational velocity of the rotating arcuate electric field. Various methods for separating ions according to their on mobility are also provided.

24 Claims, 8 Drawing Sheets

APPARATUS AND METHODS FOR ION MOBILITY SPECTROMETRY

FIELD OF THE INVENTION

This invention relates to apparatus and methods for ion mobility spectrometry (IMS), including ion mobility spectrometers. The apparatus and methods may be suitable for use in combination with mass spectrometry (MS), e.g. in hybrid IMS/MS instruments.

BACKGROUND OF THE INVENTION

Known ion mobility spectrometers typically comprise a drift tube wherein ions are caused to drift under the influence of a constant applied electric field. Various constructions of drift tube have been proposed. The drift tube may, for example, comprise a series of ring electrodes axially spaced apart along the length of the spectrometer, wherein a constant potential difference is maintained between adjacent ring electrodes such that a constant electric field is produced in the axial direction. A pulse of ions is introduced into the drift tube, which contains a buffer gas, and as the ions travel through the tube under the influence of the constant electric field they attain a constant drift velocity and separate in the axial direction according to their ion mobility. The buffer gas is often arranged flowing in the opposite direction to the direction of ion travel.

An ion mobility spectrometer may be operated on its own as a means for ion separation or it may be used in combination with other ion separation devices in so-called hybrid IMS instruments. Examples of hybrid IMS instruments include those based on liquid chromatography IMS (LC-IMS), gas chromatography IMS (GC-IMS) and IMS mass spectrometry (IMS-MS). The latter type of instrument is a powerful analytical tool which employs mass spectrometry for further separating and/or identifying peaks in an ion mobility spectrum. More than two separation techniques may be combined, e.g., GC-IMS-MS.

Ion mobility spectrometers may be operable at atmospheric pressure (see e.g. U.S. Pat. No. 5,162,649) and can offer a resolution of up to 150 (see e.g. Wu et al., Anal. Chem. 1998, 70, 4929-4938). However, operation at lower pressures is more suitable for hybrid IMS-MS instruments (see e.g. U.S. Pat. No. 5,905,258 and WO01/64320) to increase speed of separation and reduce ion losses. Operation of the ion mobility spectrometer at lower pressures frequently leads to greater diffusion losses and lower resolution. In order to counter the problem of diffusion losses, an RF pseudo-potential well may be arranged in the drift tube to confine ions radially so that it acts as an ion guide and may be used to transportions efficiently (see e.g. U.S. Pat. No. 6,630,662).

In a modification to an ion mobility spectrometer, U.S. Pat. No. 6,914,241 describes how ions may be separated according to their ion mobility by progressively applying transient DC voltages along the length of an ion mobility spectrometer or RF ion guide comprising a plurality of axially spaced apart electrodes. The ion mobility spectrometer may comprise an RF ion guide such as a multipole rod set or a stacked ring set. The ion guide is segmented in the axial direction so that independent transient DC potentials may be applied to each segment. The transient DC potentials are superimposed on top of an RF voltage which acts to confine the ions radially and/or any constant DC offset voltage. The transient DC potentials thereby generate a so-called travelling wave which moves along the length of the ion guide in the axial direction and which acts to move ions along the length of the ion mobility spectrometer.

In the above types of ion mobility spectrometers, ions are propelled along the ion guide and ions may be separated according to their ion mobility. However, in order to achieve a high resolution or resolving power of ion mobility separation at relatively low pressures, a relatively long drift tube must be employed in order to keep within the so-called low field limit as described in more detail below.

In order to separate ions along the axial direction according to their ion mobility in an RF ion guide, an axial DC electric field may be generated which is orthogonal to the radial RF field for radial confinement. If a constant axial electric field E is applied in order to move ions along and through an ion guide containing a gas, then the ion will acquire a characteristic velocity, v according to:

$$v = E^*K \qquad \text{(eqn. 1)}$$

wherein K is the ion mobility.

In order to maintain ion mobility separation in the so called low field regime wherein ions do not receive significant kinetic energy from the driving field, the ratio of E (in V/m) to the pressure of the background gas P (in mbar) should be maintained at a value less than about 200V/(m*mbar). At the same time, resolving power, R, of separation according to ion mobility (FWHH) is limited by diffusion and can be approximately estimated as:

$$R = \frac{1}{2}\sqrt{\frac{ezEL}{kT}} \qquad \text{(eqn. 2)}$$

wherein z is the charge state of ions, L is the length of separation (m), T is temperature (degrees Kelvin) of background gas, e is the elementary charge ($1.602*10^{-19}$ Coulomb) and k is Boltzmann's constant ($1.38*10^{-23}$ J/K). More accurate calculations can be found, e.g., in G. E. Spangler, "Expanded Theory for the resolving power of a linear ion mobility spectrometer", Int. J. Mass Spectrom. 220 (2002) 399-418. As increase of E is limited by low-field conditions and decrease of T is associated with cumbersome cryogenic techniques, it can be seen that the only way towards achieving higher R is to increase the separation length L. However, increasing the separation length can be problematic since space is typically limited.

One solution to the problem of increasing the separation length proposed in the prior art of WO2008/104771, GB2447330 and GB2457556 is to coil the ion mobility drift tube. However, construction of the drift tube becomes complex in that case and precludes rapid transfer of ions through the spectrometer in the case when no mobility separation is required.

It can therefore be seen that there is a need to improve ion mobility spectrometers, particularly a need to provide an ion mobility spectrometer having an increased separation length and more particularly a need to provide an ion mobility spectrometer having an increased separation length but without complex construction. In view of the above background, the present invention has been made.

SUMMARY OF THE INVENTION

According to an aspect of the present invention there is provided an ion mobility spectrometer for separating ions according to their ion mobility having at least two ion separation paths of different lengths.

According to another aspect of the present invention there is provided a method of separating ions according to their ion mobility comprising:

providing a drift tube having therein at least two ion separation paths of different lengths;

selecting one of the ion separation paths for ions to follow; and causing ions to follow the selected ion separation path and separating the ions along the selected ion separation path according to their ion mobility.

Preferably, the at least two ion separation paths are adjacent to electric field generation means, said electric field generation means being switchable between operating conditions to provide in one condition a separating electric field substantially aligned with a first path of a first length and in another condition a different separating electric field substantially aligned with a second path of a second length different to the first length.

According to an additional aspect of the present invention there is provided an ion mobility spectrometer for separating ions according to their ion mobility, having electric field generation means being switchable between operating conditions to provide in a first condition a separating electric field substantially aligned with a first path of a first length and in a second condition a different separating electric field substantially aligned with a second path of a second length different to the first length.

According to a further aspect of the present invention there is provided an ion mobility spectrometer for separating ions according to their ion mobility comprising a straight drift tube having therein a helical ion separation path.

According to a still further aspect of the present invention there is provided a method of separating ions according to their ion mobility comprising:

providing a straight drift tube;

causing ions to follow a helical ion separation path within the drift tube and separating the ions along the helical ion separation path according to their ion mobility.

According to a yet further aspect of the present invention there is provided an ion mobility spectrometer for separating ions according to their ion mobility comprising a helical ion separation path surrounding an inner axially extending electrode assembly.

According to still another aspect of the present invention there is provided a method of separating ions according to their ion mobility comprising:

providing a helical ion separation path within a drift tube surrounding an inner axially extending electrode assembly; and causing ions to follow the helical ion separation path within the drift tube and separating the ions along the helical ion separation path according to their ion mobility.

According to an additional aspect of the present invention there is provided an ion mobility spectrometer having a helical ion separation path within a drift tube for separating ions according to their ion mobility wherein a rotating arcuate electric field is applied in operation to separate ions having an ion mobility such that their rotational velocity in the drift tube is matched to the rotational velocity of the rotating arcuate electric field.

According to another additional aspect of the present invention there is provided a method of separating ions according to their ion mobility comprising:

providing a helical ion separation path within a drift tube for separating ions according to their ion mobility;

causing ions to follow the helical ion separation path within the drift tube and separating the ions along the helical ion separation path according to their ion mobility; and applying a rotating arcuate electric field within the drift tube so as to separate ions having an ion mobility such that their rotational velocity in the drift tube is matched to the rotational velocity of the rotating arcuate electric field.

Preferably, the at least two ion separation paths of different lengths of the ion mobility spectrometer comprise a first ion separation path which is straight and a second ion separation path which is helical. More preferably, the second ion separation path is longer than the first ion separation path.

Advantageously, the present invention addresses the problem of how to increase the ion mobility separation length within a limited space and with a simple construction. It can be seen that the invention in certain embodiments provides for at least two ion separation paths (i.e. ion trajectories) within one drift tube, preferably including one ion separation path which is a curved, more preferably helical, ion separation path. Such construction allows several unique modes of operation. One ion separation path, the curved or helical path for example, may provide a long separation path of high resolving power of ion mobility and lower speed. The at least one other path, which for example may be straight and for example may provide a shorter separation path of lower resolving power of ion mobility and higher speed than the helical path. The present invention in certain embodiments thus beneficially provides an ion mobility spectrometer having at least two ion separation paths of different length thereby enabling at least two different resolving powers and two different separation speeds, especially in a low field regime for the axial electric field. The invention accordingly further provides an ion mobility spectrometer and method of ion mobility spectrometry having switchable modes of speed and/or resolution. The drift tube itself is preferably straight not coiled and thus of simple construction compared to coiled drift tubes of the prior art.

The drift tube is preferably a straight drift tube and a high resolving power may beneficially be provided by a helical ion separation path within a straight drift tube wherein the drift tube is of similar length to a conventional straight drift tube, the length of the curved or helical ion separation path being substantially longer than the length of the drift tube. The invention thus enables a long separation path length, and hence high resolution of ion mobility separation, to be provided in a limited space.

In certain preferred embodiments, the present invention provides filtering of ions according to ion mobility and coupling of the filtered ions to a further ion separation and/or identification device, preferably a mass spectrometer.

Other advantages of the present invention include the possibility of rapid transfer of ions through the ion mobility spectrometer when no mobility separation is required. This could be used in combination with mobility separation, e.g. for adding internal calibrants to mobility-selected species.

Ions to be separated by the ion mobility spectrometer of the present invention are typically generated by an ion source as hereinafter described. The generated ions may be injected into the ion mobility spectrometer via an injection device, e.g. comprising ion optics, which may comprise e.g. an injection multipole.

The ion mobility spectrometer may comprise an ion storage device or section into which the ions to be separated may be introduced, e.g. after the ion source, the ion storage device or section having therein an ion storage space. The ion storage device or section accordingly preferably comprises an ion trap. The ion storage device or section is preferably for the controllable storage of the ions and release of the ions into the drift tube of the ion mobility spectrometer for separation, preferably as a pulse of ions, i.e. it is preferably a pulsed ion storage device or section. The ion storage device or section is preferably configured to provide an axial field gradient in the storage space when a voltage difference is applied between its axial ends. The axial field gradient in the storage space may thereby move ions in the storage space in the axial direction towards the drift tube of the ion mobility spectrometer for separation. The ions may be stored in the storage device or section until injection into the drift tube is required. Thus, preferably the ion storage device or section preferably allows controllable gating of ions into the drift tube, e.g. by means of a gating electrode. It can be seen from the above preferred embodiments, that the ion mobility spectrometer preferably comprises a pulsed ion injector, which may be provided for example by the described ion storage device, for pulsed injection of ions into the drift tube.

Preferably, the ion mobility spectrometer comprises a drift tube having therein the ion separation path(s). The drift tube defines therein a drift space in which the ions may be separated according to ion mobility. The drift space preferably contains a gas for ion mobility separation.

The drift tube thus comprises in certain embodiments therein a drift space in which the at least two ion separation paths are provided. More preferably, the first ion separation path is straight, and even more preferably runs substantially in an axial direction, through the drift space. More preferably, the second ion separation path is curved, more preferably helical, and even more preferably the axis of the helical path is substantially co-axial with the long axis of the drift tube. The long axis preferably lies radially at the centre of the drift tube. For axial movement of ions, preferably there is applied in the drift tube, in use, an axial electric field gradient (axial DC field). The axial electric field gradient may be provided e.g. by a DC voltage difference applied between the axial ends of the drift tube.

Preferably, the drift tube is straight. It will be appreciated that herein straight means at least substantially straight and some deviation from a strictly geometrically straight configuration is thereby allowed. The drift tube preferably comprises an outer tube extending axially. The drift tube more preferably comprises an outer electrode assembly extending axially which defines therein the drift space. Thus, in certain embodiments, the outer electrode is preferably the outer tube. The outer tube or electrode is more preferably in the form of a cylinder. The outer electrode preferably comprises a resistive material, i.e. at least on its inner surface, more preferably the outer electrode is made from resistive glass. In use, where the outer electrode is a resistive material a voltage is preferably applied between the axial ends of the outer electrode such that a voltage gradient is produced in the axial direction, which can thereby promote movement of the ions from the entrance axial end of the drift tube to the exit axial end, i.e. to promote axial motion of the ions. In other embodiments, alternatively or in addition to the outer electrode providing an axial voltage gradient, an axial voltage gradient may be provided from the inner electrode, for example from the inner electrode alone. Provision of an axial voltage gradient by the inner electrode is described in more detail below.

The ion mobility spectrometer preferably comprises an axially extending inner electrode assembly located within the drift tube. The outer electrode or tube preferably annularly surrounds the inner electrode assembly. The drift space in such embodiments is located between the outer tube or electrode of the drift tube and the inner electrode assembly, i.e. annularly around the inner electrode assembly. The inner electrode assembly is preferably located within the outer tube or electrode co-axially with the outer tube. The inner electrode assembly more preferably comprises a cylinder form. Accordingly, the drift tube most preferably comprises two co-axial cylinders wherein the drift space is located between the co-axial cylinders, the cylinders comprising an outer cylinder as an outer electrode and an inner cylinder as an inner electrode assembly. The curved or helical ion separation path in such embodiments thus is located in the drift space between the co-axial cylinders and turns around the inner cylinder.

In use, the ions are moved axially through the drift space in the drift tube by means described in more detail below. As the ions move through the drift space they become separated according to ion mobility. As the ions are moved axially, the ions are preferably radially confined. The ions are preferably radially confined in use using an RF electric field. For radial confinement, preferably there is further applied in the drift tube in use a radial electric field gradient (radial DC field), e.g. by a DC voltage difference applied between the outer electrode of the drift tube and the inner electrode assembly, e.g. with the ions being driven towards the inner electrode assembly by a DC voltage difference applied between the outer electrode of the drift tube and the inner electrode assembly. For the RF radial field, the drift tube preferably comprises one or more RF electrodes for confining the ions radially by providing the RF radial field. The RF electrodes provide an RF barrier which opposes the radial directing effect of the DC voltage difference applied e.g. between the outer electrode of the drift tube and the inner electrode assembly. The RF electrodes may in some embodiments have a combination of DC and RF applied to them in order to provide both the DC radial electric field gradient and the RF radial field. In a preferred embodiment, the inner electrode assembly preferably comprises RF electrodes spaced annularly around the central axis (i.e. long axis) of the drift tube which extend axially, preferably parallel to the long axis, i.e. in the axial direction. The RF electrodes are preferably equally spaced annularly around the central (long axis) of the drift tube. For example, the RF electrodes may be spaced annularly around the inner electrode assembly (but separated therefrom), i.e. with the ion separation paths located radially outwards of the RF electrodes. The RF electrodes, which have at least an RF voltage applied to them in use, thereby provide an RF barrier for preventing ions colliding with the inner electrode assembly, e.g. where the voltage difference applied between the outer electrode of the drift tube and the inner electrode assembly drives the ions towards the inner electrode assembly. Additionally, or alternatively, the RF electrodes may be equally spaced annularly close to the inner surface of the outer electrode assembly (but separated therefrom), whereby in use with RF applied they provide an RF barrier for preventing ions colliding with the outer electrode assembly, e.g. where the voltage difference applied between the outer electrode of the drift tube and the inner electrode assembly drives the ions towards the outer electrode assembly. The RF electrodes may conveniently comprise wires. In use, adjacent pairs of the RF electrodes are preferably provided with opposite phase RF voltages. It thus can be seen from the foregoing that ions may be radially confined in the drift tube in use by applying a radial DC field in combination with an RF field in the drift tube applied by means of one or more RF electrodes coupled to the inner electrode assembly and/or outer electrode assembly.

In another preferred embodiment, ions are radially confined in the drift tube in use by applying an RF field to the entire inner electrode assembly and thereby creating a quasi-potential in the drift tube, wherein the RF is coupled to the inner electrode assembly by means of one or more RF electrodes located within the inner electrode assembly. Similarly, RF could be coupled to the outer electrode assembly thereby creating a quasi-potential in the drift tube by means of an RF electrode or electrodes located in proximity to the outer electrode assembly. The total combined effect of the radial field effects described above is such that in the drift tube there is a radial electric field having a potential minimum at a radius within the drift space, thereby providing radial confinement towards the said potential minimum.

The switchable electric field generation means comprise one or more electrodes as hereinafter described.

The ion mobility spectrometer preferably comprises in use an axial electric field to drive the ions axially in the drift tube, i.e. along the long axis of the drift tube. For this purpose, the ion mobility spectrometer preferably comprises an axial driving electrode, which is preferably a resistive electrode, for providing an axial driving force to the ions, i.e. to drive the ions axially in the drift tube. The axial driving electrode may be continuous or segmented. Where the axial driving electrode is segmented in particular, it need not be resistive but may be made of conductive material with stepped voltages applied between successive segments in order to provide an axial electric field. The axial driving electrode may be linear or more preferably is helical as described in more detail below, in either case extending in the axial direction. In some embodiments, the outer electrode of the drift tube, which may be resistive, may form the axial driving electrode, at least in part. Where the axial driving electrode is helical it preferably extends axially along the drift tube, with the helix it forms having its axis substantially co-axial with the long axis of the drift tube.

The ion mobility spectrometer preferably comprises at least one guiding electrode for providing a guiding potential barrier to direct the ions along a separation path other than a straight path, e.g. to direct the ions along a helical path. Accordingly, in such embodiments, the guiding electrode is preferably a curved electrode, a helical electrode being most preferred. The path provided by the guiding electrode, preferably helical, is longer than a straight path through the drift tube and accordingly as the ions follow the path provided by the guiding electrode they become separated with greater resolution than if they followed a straight path through the drift tube. Where the guiding electrode is helical it preferably extends axially along the drift tube, more preferably with the helix it forms having its axis substantially co-axial with the long axis of the drift tube. The guiding electrode may be continuous or segmented. The guiding electrode is preferably for applying a switchable voltage thereto, thereby permitting the guiding potential barrier to be switched on or off. This feature advantageously enables two separation paths to be provided within the drift tube, e.g. a path with the guiding potential barrier switched off (e.g. such as the straight path) and a path with the guiding potential barrier switched on (e.g. such as the helical path). Where both are present, the helical axial driving electrode and the helical guiding electrode are arranged to form a double helix, preferably with the axis of the double helix being substantially co-axial with the long axis of the drift tube. In certain preferred embodiments the helical guiding electrode is wound around the inner electrode assembly. The guiding electrode may be conductive or resistive, preferably resistive.

The inner electrode assembly preferably further comprises an inner support, especially a cylinder, which more preferably extends axially along the length of the drift tube. This inner support or cylinder is preferably made of a dielectric material.

The inner support or cylinder preferably carries thereon the axial driving electrode and/or the guiding electrode as described above and in more detail below. However, in certain embodiments, the outer cylinder may additionally or alternatively carry thereon (e.g. on its inner surface) an axial driving electrode and/or a guiding electrode as described above and in more detail below.

Preferably, especially for use in high-resolution separation modes, the spectrometer comprises arcuate field electrodes, which preferably extend axially along the drift tube and are positioned around the long axis of the drift tube, i.e. arcuately spaced around the long axis. The arcuate field electrodes preferably are equally arcuately spaced about the long axis. The arcuate field electrodes may conveniently be provided in the form of conductive strips. The arcuate field electrodes may be present at the inner surface of the outer tube or electrode of the drift tube, or at the outer surface of the inner electrode assembly. The arcuate field electrodes preferably extend parallel to each other, more preferably as they extend axially. In use, preferably each arcuate field electrode has a switchable voltage independently applied to it, thereby providing an arcuate electric field. The arcuate field is a rotating rather than static field which is achieved by progressively applying the independent switchable voltages to the arcuate field electrodes, i.e. in the form of a transient waveform.

At the exit of the drift tube, i.e. after the ions have become separated according to ion mobility, the separated ions are extracted from the drift tube, e.g. via an exit gate electrode allowing for pulsed extraction. After the ions are extracted, they may proceed to one or more further stages of ion processing (e.g. mass spectrometry, such as mass filtering, ion storage and/or mass analysis, with or without ion fragmentation) and/or detection. For example, various hybrid instrument configurations may incorporate the ion mobility spectrometer of the present invention, such as IMS/MS or IMS/MS/MS or IMS/(MS)$^n$, where IMS denotes a stage of ion mobility spectrometry of the present invention and MS a stage of mass spectrometry.

The ion mobility spectrometer of the present invention may be operated in various different modes.

In one mode of operation, a so-called transmission mode, ions are allowed to drift through the drift tube being pulled by the axial field but without ion mobility separation. In other words, the spectrometer thus acts as a simple ion guide in this transmission mode.

In a low resolution mode of operation for ion mobility separation, which may provide a resolution of ion mobility separation similar to existing straight path ion mobility spectrometers, the spectrometer is operated in the manner of the transmission mode except that ions are preferably injected as a pulse into the drift tube and the ions are separated by ion mobility as they travel through the drift tube. In this low resolution mode, the guiding electrode has its voltage switched off, or set low, so that there is substantially no potential barrier influencing the axial motion of the ions: Accordingly, in this low resolution ion mobility separation mode, the ions drift axially substantially straight through the drift tube.

In a high resolution mode of operation for ion mobility separation the high resolution mode makes use of the guiding electrode to provide a separation path of longer path length, i.e. higher resolving power, preferably a helical separation path. In the high resolution mode, as with the low resolution mode, the ions are preferably injected as a pulse into the drift tube and the ions are separated by ion mobility as they travel through the drift tube under the influence of the axial electric field gradient. The guiding electrode has its voltage switched on so that there is an electrical potential barrier restricting pure axial motion of the ions and the ions must instead follow the potential barrier, which is preferably helical based on a helical guiding electrode. The high resolution mode is preferably operated with a rotating arcuate electric field applied within the drift tube. Accordingly, the arcuate field electrodes are preferably operated in this mode such that voltages are independently applied to them in a progressive manner to provide a rotating arcuate electric field (i.e. a field in the arcuate direction) to drive ions within the arcuate electric field in the arcuate direction. The rotating arcuate electric field is preferably provided so that it spans a sector (i.e. in the arcuate direction) of less than 360 degrees, e.g. 240 degrees. This may be achieved by applying appropriate voltages, preferably substantially the same voltage, to two out of three equally arcuately spaced arcuate field electrodes with a different or no voltage on the remaining one of the strips. The rotational velocity (i.e. in the arcuate direction) of the rotating arcuate field is preferably synchronised with the rotational velocity of ions of a selected ion mobility, K, i.e. so that the rotating arcuate field and the ions of the selected ion mobility are in phase, so that such ions are moved through the drift tube along the helical path whereas ions of other ion mobility become out of phase with the arcuate field and consequently may be slowed down or lost in the spectrometer. This rotating electric field can be employed to provide a filtering effect so that only ions of selected ion mobility are transmitted through the spectrometer with other ions being filtered out. In the high resolution filtering mode the electric field in the sector outside the rotating arcuate field is preferably a defocusing field so that ions in this remaining sector become lost on a wall of the drift tube. The defocusing field may be provided e.g. by a DC radial field gradient directing ions to become lost on a wall of the drift tube. The high resolution mode can alternatively be operated with trapping so that ions which have a rotational velocity slower or faster than, i.e. out of phase with, the rotating arcuate electric field nevertheless remain trapped in the drift tube. The said trapped ions may remain trapped in the drift tube, for example by a DC radial field gradient in the remaining sector directing ions to remain within the drift tube, for example until the rotational velocity of the arcuate field is changed to match the rotational velocity of the trapped ions, and hence the said trapped ions can then be transmitted through the drift tube.

The duty cycle of the ion mobility spectrometer may be increased by injecting ions into the ion mobility spectrometer at the same phase of subsequent cycles of the rotating arcuate field, more preferably every subsequent cycle of the rotating arcuate field.

In one type of operation mode, a mass spectrometer may be arranged to detect ions extracted from the ion mobility spectrometer of selected ion mobility having one or a limited number of m/z values so that the instrument thereby provides an ion specific detector. In a more typical mode of operation, a mass spectrum is obtained by a mass spectrometer for each of a plurality of narrow ranges of ion mobilities transmitted by the ion mobility spectrometer (i.e. a mass spectrum is obtained for each ion mobility peak, thereby resolving a single ion mobility peak into its m/z components). A two-dimensional (2D) mobility/mass diagram can be obtained in this way. Another preferred method is a so-called linked-scan method, which allows selection only of ions of certain type (s), e.g. peptides only, which can greatly improve the dynamic range of analysis of complex mixtures and avoid analysing analytically useless ions (e.g. singly-charged and polymers ions in the case of peptide mixtures). In the linked-scan method, a mass filter, e.g. quadrupole mass filter, positioned downstream of the ion mobility spectrometer is scanned simultaneously with the mobility scanning by the ion mobility spectrometer so that only ions of pre-determined mobility/mass ratio or lying on a pre-determined curve on a mobility/mass diagram are selected for subsequent processing or detection, e.g. mass analysis, with or without an intermediate fragmentation of the selected ions. The selected ions of pre-determined mobility/mass ratio or lying on a pre-determined curve on a mobility/mass diagram in this way are preferably accumulated in an ion trap before subsequent mass analysis, e.g. by an FT mass analyser that measures the frequency of oscillation induced by a potential that varies harmonically in one direction (e.g. an Orbitrap™ mass analyser) or a TOF mass analyser. The space charge capacity of the ion trap can be utilised to the full since only ions of interests are selected and accumulated in the trap. In such an operation, a high-resolution mass spectrum, such as obtained using an Orbitrap™ analyser, can be obtained which will include only ions of interest (e.g. 2- or 3-charged ions, or glycopeptides only, etc.) and therefore the space charge capacity of the trap or analyser is utilised to the full. One or more scans can be taken at different mobility/mass ratios or along different curves on a mobility/mass diagram.

It will be appreciated that the spectrometer of the present invention may be suitable for the transmission and separation of either positively or negatively charged ions. The voltages applied to the various electrical components simply need to have their polarities reversed in order to transmit and separate ions of the opposite polarity.

It will be appreciated that further modifications to the present invention may be made to incorporate features of ion mobility spectrometers of the prior art. For example, according to certain embodiments of the present invention, an arcuate field is applied which rotates, i.e. is applied as a so-called travelling wave. The feature of applying the axial field gradient as a travelling wave in order to further filter the ions according to their ion mobility as described in the prior art (e.g. U.S. Pat. No. 6,914,241) may also be employed. For this purpose the axial field gradient or axial driving electrode is preferably of segmented form so that potentials may be applied progressively applied to successive segments to thereby provide a travelling wave axial field gradient.

DETAILED DESCRIPTION OF THE INVENTION

In order to more fully understand the invention, it will now be described by way of example with reference to the accompanying Figures in which.

Figure 1:
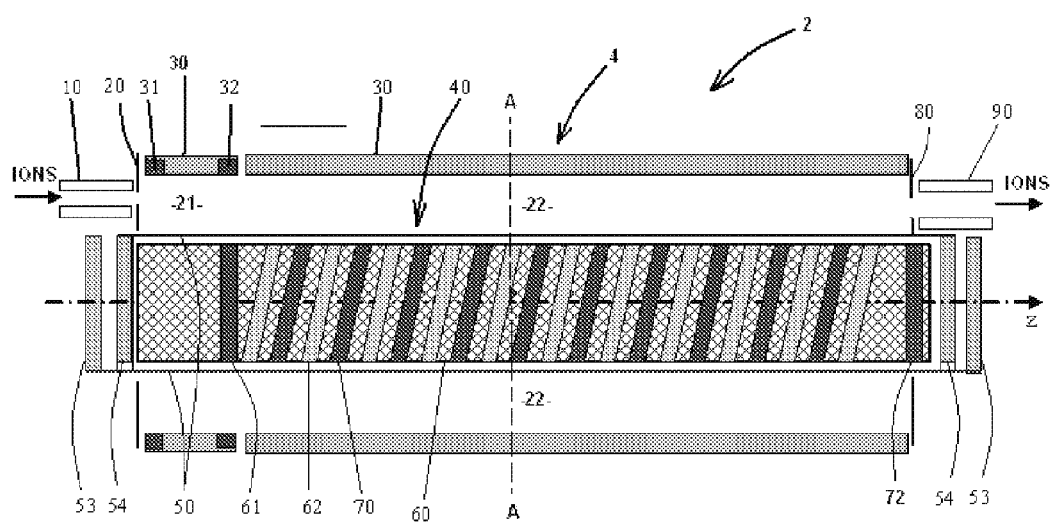
FIG. 1 shows schematically a side view, partly in cross section, of an embodiment of an ion mobility spectrometer according to the present invention taken on the line B-B shown in FIG. 2.
Figure 2:
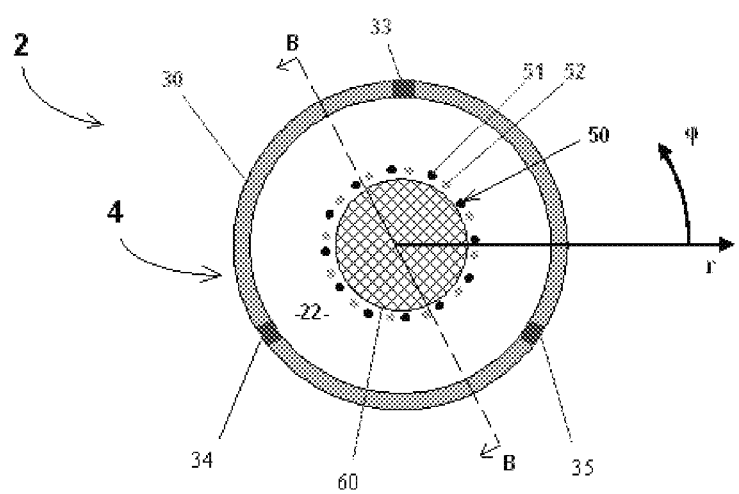
FIG. 2 shows schematically a transverse cross-sectional view of the embodiment shown in FIG. 1 taken on the line A-A.

Referring to FIGS. 1 and 2, there are shown schematically, and thus not to scale, a partly sectional side view and a transverse sectional view respectively of an embodiment of an ion mobility spectrometer 2 according to the present invention. The FIGS. 1 and 2 indicate the directions of the polar coordinates, z, r and $\phi$.

Ions to be separated by the spectrometer 2 are generated by an ion source (not shown), which may be any suitable type of ion source, and which may be any conventional type of ion source, e.g. an electrospray ionization (ESI), matrix assisted laser desorption ionisation (MALDI) or another type of ion source. The ions generated by the source may enter the spectrometer 2 in use via an injection device, which typically comprises ion optics, which in the shown embodiment comprises an injection multipole 10. In other embodiments, the injection device could comprise any RF transmission or storage device such as an elongated set of rods, apertures, spirals with or without bath gas. The ions injected from the injection device enter the spectrometer via an entrance aperture or 20 therein. Entrance aperture 20 acts as an ion gate and may have a switchable voltage applied to it to selectively either allow ions to pass through it (gate open) or not pass through it (gate closed).

The spectrometer 2 comprises a drift tube 4, which in the embodiment shown comprises an outer electrode, in this case in the form of cylinder 30, which is elongated in the axial direction, z, which is the long axis of the tube. In FIG. 1, the cylinder 30 is shown in an axial cross section. The length of the cylinder 30 in the embodiment is 200 mm and its inner diameter is 60 mm. The cylinder 30, as shown in FIG. 2, is a circular cylinder but need not be. The cylinder 30 could, for example, comprise another type of cross section shape such as elliptical or some other curved shape, although a circular cylinder is preferred. The electrode cylinder 30 is made of resistive glass in the embodiment but could be made of another resistive material. Resistive glass drift tubes for ion mobility spectrometry are known. In other embodiments, the cylinder 30 may comprise a resistive material only on its inner surface. In use, when a voltage of 50-200 V is applied between the ends of cylinder 30 (i.e. opposite axial ends) a voltage gradient is thus produced in the axial direction, which can assist moving the ions from the entrance end of the drift tube to the exit end, i.e. the axial motion of the ions.

Figure 11:
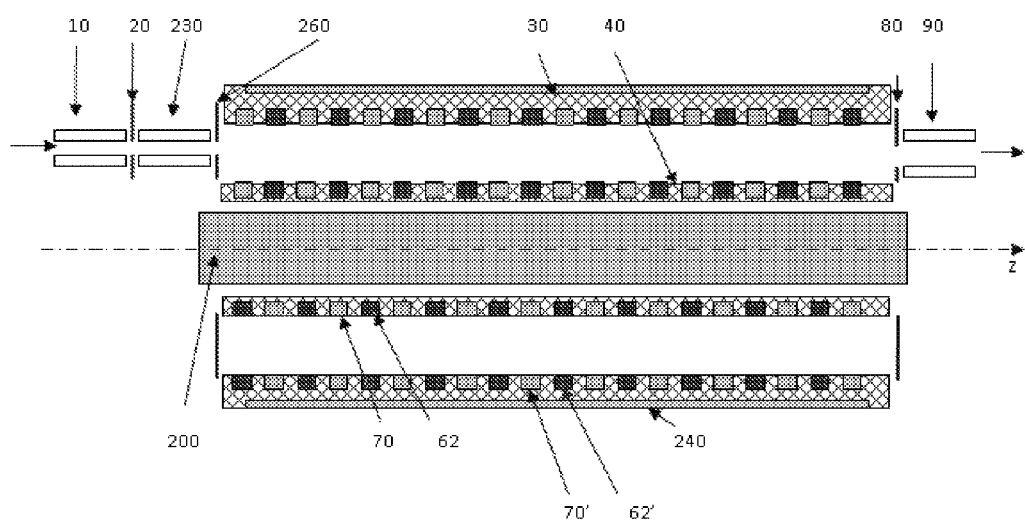
FIG. 11 shows schematically a side view, in cross section, of another embodiment of an ion mobility spectrometer according to the present invention.

The spectrometer in the embodiment shown comprises a storage section $30^I$, which may be an electrically insulated portion of resistive cylinder 30, or another cylinder comprising resistive material (at least on its inner surface), of the same diameter and co-axial with cylinder 30 electrically insulated from the main portion of cylinder 30 in which separation of ions occurs. In other embodiments, however, such as shown in FIG. 11 described below, the storage section need not comprise a co-axial cylinder, co-axial with the main cylinder 30 of the drift tube since the storage section needs only to provide a region for the storage of ions prior to releasing the ions, preferably as a pulse, into the drift tube 4. The ions from the injection device initially enter the storage section $30^I$ via the aperture 20. The storage section $30^I$ defines therein a storage space 21, which in the example shown is an annular storage space (although as indicated above it need not be annular, e.g. in cases where the storage section does not comprise a co-axial cylinder), in which the ions may be stored before selected gating of the ions into the separation portion of cylinder 30, i.e. into drift space 22. The storage section $30^I$ preferably comprises resistive material, at least on its inner surface, and carries in electrical connection therewith two electrodes, in this example in the form of annular conductive strips 31, 32, located respectively at each end of the storage section $30^I$ to provide an axial electric field gradient when a voltage difference of 5-50 V is applied between the electrodes or strips 31, 32, which in this example are annular electrodes. In use the ions move in the axial direction towards the separation portion of cylinder 30 under the influence of the axial gradient in the storage section $30^I$. The ions may be held in the storage section $30^I$ and controllably gated into the separation portion of cylinder 30 by means of a voltage applied to a gating electrode 61 described in more detail below.

The spectrometer has located within the outer cylinder 30 an inner electrode assembly 40. The electrode assembly 40 is co-axially mounted with respect to the outer cylinder 30. The drift space 22 in which the ions are separated by ion mobility in use thereby comprises the annular volume between the outer cylinder 30 and inner electrode assembly 40. The drift space 22 is occupied in use with a gas. The gas may be any gas conventionally used for ion mobility spectrometry (such as nitrogen, helium, methane, etc. or any mixture of them. The gas may be provided in the drift space at pressures known in the art to be useful for ion mobility spectrometry, e.g. at atmospheric pressure, or above or below atmospheric pressure. Preferably, however, the gas is provided at atmospheric pressure or below. More preferably, the gas is provided below atmospheric pressure, still more preferably at 0.005 to 20 mbar, and most preferably at 0.1 to 1 mbar. The gas may be arranged to flow in the drift space, e.g. counter to the direction of ion movement, but preferably and for simplicity the gas is not arranged to be flowing.

The electrode assembly 40 comprises RF electrodes 50 equally spaced annularly around the z or long axis of the drift tube and running parallel to the z axis, i.e. in the axial direction. In the embodiment the RF electrodes 50 are conveniently provided in the form of wires which are stretched across holders 53, 54. In use, adjacent wires, e.g. 51, 52 shown, are provided with opposite phase RF voltages to form an RF quasi-potential. In FIG. 2, each wire with the same shading is given the same phase of the RF voltage. The RF electrodes 50 thereby provide an RF barrier to stop ions from falling into electrode assembly 40. The ions in use are radially confined by being urged towards the inner electrode assembly 40 and its RF barrier by a DC voltage difference applied of 1 to 20 V between the outer cylinder 30 and the electrode assembly 40.

The electrode assembly 40 further comprises an inner cylinder 60 running the length of the spectrometer and drift tube. The cylinder 60 is preferably made of a dielectric material, preferably glass (e.g. lead silicate) or ceramics. The outer diameter of cylinder 60 is 50 mm. The inner cylinder 60 acts to support both a gating electrode, in this case in the form of an annular conductive strip 61, and a guiding electrode, in this case in the form of resistive strip 70, helically wound around the cylinder 60. In the embodiment shown, the inner cylinder 60 further supports an axial driving electrode, in this case in the form of a resistive strip 62 also helically wound around the cylinder 60. For simplicity, neither resistive strip 70 nor resistive strip 62 described below are shown in the transverse sectional view of FIG. 2. The annular conductive band 61 surrounds the circumference of the cylinder 60 and is axially positioned at the exit of the storage space 21. In the embodiment shown, the annular conductive band 61 is axially positioned level with the conductive strip 32. When a switchable gate voltage is applied to the annular conductive band 61 in use it acts as a gating electrode to gate ions from the storage space 21 into the drift space 22 wherein the ions are to be separated by ion mobility. Annular conductive band 61 thus has a switchable voltage applied to it to selectively either allow ions to pass through it (gate open) or not pass through it (gate closed). The resistive strip 70 is helically wound around the cylinder 60 in the axial direction along the length of the cylinder 60. The resistive strip 70 is for applying a switchable DC voltage thereto. When a voltage is applied to the resistive strip 70 a helical potential barrier is thereby provided to the axially moving ions as described in more detail below. The conductive strips or components described herein are preferably made of a metal, such as nickel, tungsten, or gold for example. The resistive strip 62 and 70 is preferably made by hydrogen reduction of lead silicate glass as known in prior art or by sputtering ultra-thin layers of tungsten or other resistive metals on glass or ceramics. It is also feasible to make strips by injection molding of conductive plastic such as Sintimid, Tecaform, Semitron and others.

The inner cylinder 60 further supports a resistive strip 62 which is also helically wound around the cylinder 60. The resistive strip 62 is helically wound around the cylinder 60 in the axial direction along the length of the cylinder 60. The helix of the resistive strip 62 and the helix of the resistive strip 70 are arranged in the embodiment to form a double helix configuration, i.e. they are two congruent helices. The helix of the resistive strip 62 and the helix of the resistive strip 70 thus have substantially the same pitch of 10 mm thus resulting in 20 turns along the drift tube 4 (not all turns shown in the schematic figures). The helix of the resistive strip 62 and the helix of the resistive strip 70 are preferably translated in the axial direction with respect to one another approximately half-way along the helix pitch. The radius of either (or both) helix is preferably constant but could vary so as to provide one or more sections of increasing or decreasing radius along the axial direction, thus providing a spiral configuration. Accordingly, herein the term helical and like terms, such as helix, refer to either a strict helical shape with fixed radius or a spiral with increasing and/or decreasing radius.

Typically, the pitch or axial step of the helix is several times larger than the gap between the cylinder 60 and the RF electrodes or wires 50. The pitch or axial step of the helix is thus typically comparable with the gap between the outer cylinder 30 and the inner electrode assembly 40. For example, for a gap of 5 mm between inner cylinder 40 and outer cylinder 30 and diameter 50 mm of inner cylinder 40, gain in separation length could reach >15 to 30 comparing to the low-resolution mode, hence factor x4 to x5 gain in resolution. This is derived from the dimensions of helix pitch, P=10 mm, diameter D=50 mm of cylinder 40 and total length of tube, L=200 mm, so the gain in separation length over L equals $\pi*D/P=15.7$, with total length 3.14 m.

Figure 10:
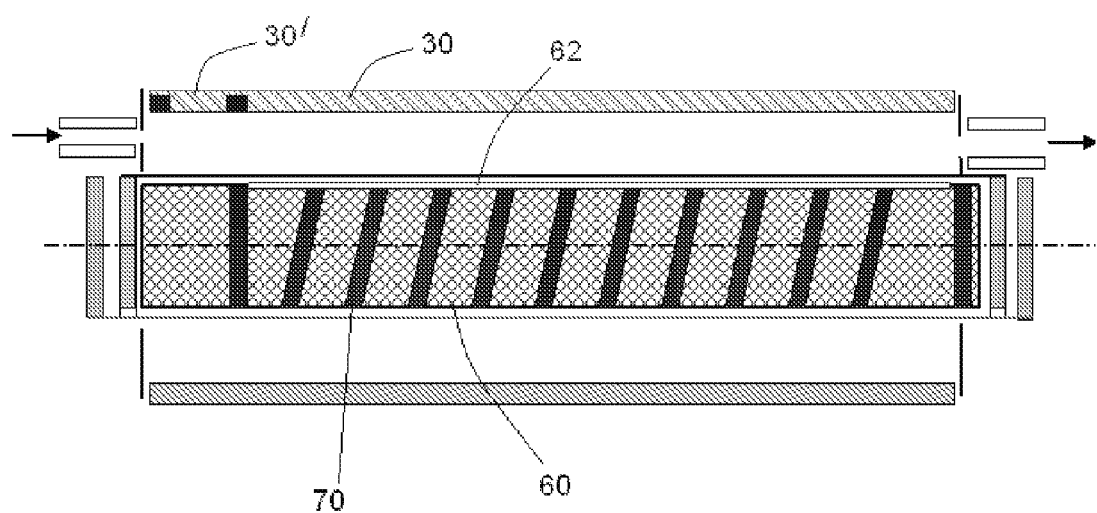
FIG. 10 shows a similar view to FIG. 1 of a further embodiment according to the present invention.

The resistive strip 62 is for applying a switchable voltage of 20 to 500 V thereto. A similar voltage distribution is created on strip 70 but shifted by 2 to 20 V according to the polarity of ions (up for positive, down for negative). When a voltage is applied to the resistive strip 62 an axial electric field gradient is thereby provided along it and an axial electrical field is generated in the drift space 22 to move the ions axially through the drift space 22 as described in more detail below. As the resistive strip 62 is for providing an axial field gradient to move the ions axially through the drift space 22, it is possible to use a resistive strip which is of some other configuration than helical. For example, resistive strip 62 in some embodiments may be in the form of a straight strip running in the axial direction along the inner cylinder 60. Such an embodiment is shown in FIG. 10 (FIG. 10 also shows storage section $30^I$ as a section of cylinder 30). However, in view of the helical resistive strip 70, the resistive strip 62 is preferably helical and more preferably forming a double helix with resistive strip 70. Where the resistive strip 62 is helical non-axial (i.e. arcuate) field components are dominated by the resistive strip 70 and also arcuate field electrodes 33-35.

In addition to the helical strip 70, for providing a further arcuate driving force to the ions, and especially for use in high-resolution separation modes, the spectrometer comprises arcuate field electrodes, in this case in the form of conductive strips 33, 34 and 35, which are present at the inner surface of the outer cylinder 30 of the drift tube 4. The conductive strips 33, 34 and 35 are made of conductive material and extend parallel to each other axially along the length of the drift tube 4, i.e. they extend axially along the inner surface of the outer cylinder 30. The conductive strips 33, 34 and 35 extend axially for substantially the same axial length as the helical resistive strip 70. The strips 33, 34 and 35 are equally arcuately spaced about the z or long axis of the drift tube and each strip in use has a switchable voltage of 1 to 20 V independently applied to it for providing a rotating arcuate electric field, which is described in more detail below. It will be appreciated that a greater number of strips than the three strips 33, 34 and 35 could be provided. Any of the conductive strips described herein, e.g. strips 31-35, 61, may each be provided as a continuous strip or as a discontinuous strip, i.e. in sections. Similarly, resistive strip 62 may be provided as a continuous strip or as a discontinuous strip, i.e. in sections.

At the exit end of the drift tube 4, i.e. at the exit end of the outer cylinder 30, the ions can exit from the drift space 22 via an exit aperture 80. Ions emerging through the exit aperture 80 may be subjected to further processing and/or detection. In the embodiment shown, a guiding multipole 90 is provided downstream of the exit aperture 80 to take ions as they exit from the drift tube. A switchable gate voltage on aperture 80 may be used to gate the ions of desired mobility before they go via multipole 90 into further stages of processing and/or detection. Exit aperture 80 thus acts as an ion gate and may have a switchable voltage of 1 to 10V applied to it to selectively either allow ions to pass through it (gate open) or not pass through it (gate closed). Preferably, as shown in FIG. 1, an annular conductive strip 72 is further provided as a means to direct ions to the aperture 80. Annular conductive strip 72 thus has a switchable voltage of 5 to 50 V applied to it to selectively either allow ions to pass through it (gate open) or not pass through it (gate closed).

Various operations of the spectrometer 2 will now be described.

Ions can be introduced into the spectrometer 2 as follows. After ion generation in an ion source (not shown) and optionally any pre-processing of the ions, such as, for example, ion storage, mass filtering and/or fragmentation, the ions are directed via the injection multipole 10 to be injected into the spectrometer. For injection, the voltage on entrance aperture or gate 20 is set (e.g. to zero or low value) to allow ions to pass through it and the ions enter the storage space 21, i.e. in the example the annular volume between the storage section $30^I$ and the inner electrode assembly 40 which is axially between the entrance aperture 20 and the conductive strip or gate 61. The ions can drift out of the storage space 21 when the conductive strip 61 which acts as a gate out of the storage space 21 has a gating voltage of 5 to 50 V switched off and set to the same voltage as the beginning of strip 62 so that ions are allowed to drift out of the storage space 21 into the drift space 22 by the axial field provided by the voltage drop between strips 31 and 32 and along strip 62. The ions then begin transmission through the drift space 22.

In one mode, a so-called transmission mode, ions are allowed to drift along the drift tube 4 through the drift space 22, being pulled by an axial field, i.e. from resistive strip 62 provided by a voltage of 50 to 200 V applied to it, but with limited ion mobility separation. In other words, the spectrometer thus acts rather as a simple ion guide in this mode. In the transmission mode the ions are typically not stored and released from the storage space 21 but rather are continuously transmitted through the spectrometer 2 and its drift tube 4. Accordingly, the drift tube 4 may be either occupied by a gas at a significant pressure for ion mobility separation or under a high vacuum. Since strip 62 is helical, the ions experience a small axial field all the time through drift tube 4 no matter where around the inner electrode assembly 40 the ions are. The ions are confined radially by applying a DC voltage difference of 2 to 20 V between the resistive outer cylinder 30 and the electrode assembly 40, e.g. by applying the resistive strip 62 with a different DC voltage to the resistive outer cylinder 30. For example, the resistive strip 62 may be applied a more negative DC voltage than the resistive outer cylinder 30 to radially confine positively charged ions (and vice versa). As the ions travel axially through the drift tube, the ions are prevented from colliding with inner electrode assembly 40 by applying RF voltage of 200 to 1000V at 3 MHz to the RF electrodes 50 as described above. In this transmission mode the helical resistive strip 70 has its voltage set to match voltages on strip 62, so that there is substantially no helical potential barrier influencing the axial motion of the ions and instead a smooth linear axial field component is sustained. Accordingly, the ions drift axially through the drift tube 4 in a substantially straight path (subject to any diffusion). Ions are confined in arcuate direction near e.g. electrode 33 by applying higher voltages to electrodes 34 and 35. In other words, the transmission mode of operation provides that the ions drift through the drift tube 4 in a non-helical straight path. The ions eventually reach the exit aperture 80 which has a voltage applied to it in transmission mode to allow the ions to pass out of the drift tube 4 and through multipole 90 for optional further processing in any downstream devices (not shown), e.g. one or more mass filters and/or ion traps, and detection.

In a low resolution mode of operation for ion mobility separation, which may provide a resolution of ion mobility separation similar to existing straight path ion mobility spectrometers, the spectrometer 2 is operated in the manner of the transmission mode except that ions are not continuously flowed through the spectrometer but rather the ions are stored and released as a pulse into the drift tube 4. This can be performed by first introducing the ions into the storage space 21 as described above. For introducing ions into the storage space, the axial field gradient within the storage space 21 is preferably applied, e.g. from strips 31, 32, to assist drift of ions into the storage space. In one operating mode for ion injection into the drift tube, the conductive strip 61 which acts as a gate out of the storage space 21 initially has a voltage of 5 to 50 V applied to it set so that ions are stopped by it and thus trapped and stored in the storage space 21. In addition, after allowing ions to enter the storage space 21, the entrance aperture 20 may have an additional voltage of few volts applied on it to trap ions within the storage space and also prevent entry of further ions into the storage space from device 10. Once the ions are within the storage space 21, it is possible, although not necessary, to switch off the axial gradient within the storage space so that the ions are stopped in the storage space. In such a mode of operation it may not be necessary for the gating electrode 61 to act to stop the ions since the absence of the axial gradient within the storage space 21 may itself be sufficient to stop the ions within the storage space. Upon applying a gating pulse on strip 61, and/or upon applying the axial field gradient in the storage space 21, the stored ions are allowed to drift out of the storage space 21 into the drift space 22, e.g. by the axial field provided by the voltage drop between strips 31 and 32.

The pulse of ions then begins transmission through the drift space 22 as above and the ions are separated by ion mobility as they travel through the drift space. A gas for ion mobility separation occupies the drift space 22 in this mode. The gas may be at atmospheric pressure or reduced pressure, preferably 0.005 to 20 mbar, more preferably 0.1-1 mbar. The axial field within the drift tube and drift space 22 is again provided by the voltage applied to the helical resistive strip 62 and optionally to the outer resistive cylinder 30. Radial confinement and RF voltage application is provided in the manner described above for the transmission mode. In this low resolution mode, the helical resistive strip 70 has its voltage set to match voltages on strip 62, so that there is substantially no helical potential barrier influencing the axial motion of the ions. Accordingly, in this low resolution ion mobility separation mode, the ions drift axially through the drift tube 4 and its drift space 22 in a substantially straight path (subject to any diffusion), i.e. between the entrance aperture 20 and the exit aperture 80. In other words, the low resolution ion mobility separation mode provides that the ions drift through the drift tube 4 in a non-helical path. The drift time through the drift tube in the low resolution mode may be typically few ms After separation according to ion mobility the ions eventually reach the exit aperture 80 which has a switchable extraction voltage 1 to 10 V applied to it to extract the ions out of the drift tube through the exit aperture. With the exit aperture 80 set to allow the ions to pass out of the drift tube 4 and through multipole 90, the ions separated according to their ion mobility can be passed to optional one or more further stages of processing and/or detection. For example, the ions may be passed to any downstream devices (not shown), e.g. one or more mass filters and/or ion traps, and detection. The exit aperture 80 can be operated with a switchable voltage to gate ions only of desired ion mobility to the further stages. Accordingly, the ions may be extracted through the exit aperture 80 either in a static (i.e. continuous) mode wherein the exit aperture has an extraction voltage continuously applied to it or in a pulsed mode wherein an extraction voltage on exit aperture 80 is pulsed to allow pulsed extraction for selecting of certain mobility value or values.

The spectrometer of the present invention may also be operated in a high resolution mode for ion mobility separation, or more specifically a variety of high resolution modes as described in more detail below, which provides a higher resolution of ion mobility separation than the low resolution mode described above. Whereas, the low resolution mode makes use of a straight separation path through the drift tube, the high resolution mode makes use of a helical separation path through the drift tube. Accordingly, the separation path in the case of the high resolution mode is longer allowing for greater separation of ions by ion mobility. The resolution of the high resolution mode may accordingly be higher than for a conventional straight path ion mobility spectrometer with the same overall dimensions of drift tube. For example, for a gap of 5 mm and diameter 50 mm, gain in separation length could reach >15 to 30 comparing to the low-resolution mode, hence factor x4 to x5 gain in resolution. Alternatively, this gain could be traded-in in exchange for a lower operating pressure (and hence lower electric field strength, E). Lower operating pressures may be beneficial, for example, when interfacing an ion mobility spectrometer to a mass spectrometer requiring a high vacuum. The drift time through the drift tube 4 in the high resolution mode may be typically between several ms to several tens ms depending on pressure and voltages.

In the high resolution mode, the spectrometer 2 is operated in the manner described above for the low resolution mode for the injection of ions and the storage and release of the pulse of ions from the storage space 21. The pulse of ions then begins transmission through the drift space 22 for the ions to be separated by ion mobility as they travel through the drift space. A gas for ion mobility separation occupies the drift space 22 in this mode. The axial field to move the ions from the entrance end of the drift tube 4 to the exit end of the tube through drift space 22 is again provided by the voltage applied to the helical resistive strip 62 and optionally to the outer resistive cylinder 30. Radial confinement, including RF voltage application to the wires 50, is again provided in the manner described above. However, in the high resolution mode, in contrast to the low resolution mode, the guiding electrode or helical resistive strip 70 has its voltage elevated by 2 to 20 V so that there is a helical electrical potential barrier restricting pure axial motion of the ions as now explained in more detail.

Figure 3:
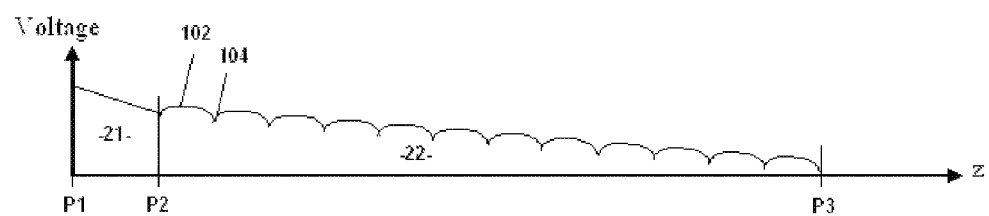
FIG. 3 shows the DC voltage profile in the axial (z) direction within the ion mobility spectrometer in one embodiment of operation.
Figure 4:
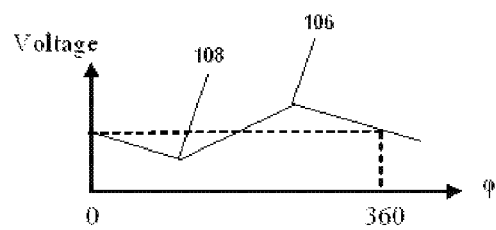
FIG. 4 shows the DC voltage profile in the arcuate ($\phi$) direction within the ion mobility spectrometer in one embodiment of operation.

The potential barrier provided by the voltage on helical resistive strip 70 is illustrated by the DC voltage profile plots shown in FIGS. 3 and 4. FIG. 3 shows the DC voltage or potential as a function of the z coordinate, i.e. in the axial direction along the long axis of the spectrometer, for fixed radial and arcuate positions (i.e. fixed r and $\phi$ coordinates). The positions P1 and P2 in the z or axial direction correspond respectively to the axial positions of the entrance and exit ends of the storage space 21, i.e. approximately to the positions of electrodes 31 and 32. P2 also marks the axial position of the entry to the drift tube 4 and drift space 22. Position P3 corresponds to the exit from the drift tube 4 and drift space 22. The axial positions of the storage space 21 and separation drift space 22 are shown for further clarity. It can be seen that there is a generally downward sloping axial potential gradient along z (and hence electric field gradient). The downward sloping axial gradient moves positively charged ions towards the exit of the drift tube and it will be appreciated that by sloping the gradient in the opposite direction that negatively charged ions could be moved towards the exit instead. The axial potential gradient is substantially linear between P1 and P2, i.e. within the storage space 21, due to the potential difference applied between electrodes 31 and 32 across the resistive cylinder 30′. The axial potential gradient between P2 and P3 on the other hand comprises a downward sloping axial potential gradient having superimposed thereon a series of potential humps corresponding to the periods of the helix formed by the helical guiding electrode or resistive strip 70. In the axial direction, for a fixed r and $\phi$, the potential rises to a local maximum (i.e. the top of a hump, the first one of which is indicated at 102) at points where the resistive strip 70 is nearest (i.e. where it passes on the near side of the cylinder 60). The minima between the humps, the first one of which is indicated at 104, correspond to points in the axial direction above strip 62 where the resistive strip 70 is furthest away. FIG. 4 shows, the DC voltage or potential profile in the arcuate or angular direction, $\phi$, for a fixed radial and axial position (i.e. fixed r and z coordinates) when the same voltages are applied to strips 33 to 35 so that any arcuate potential distribution comes only from strips 62 and 70. It can be seen that the potential around angular direction, $\phi$, for fixed r and z, rises to a local maximum, indicated at 106, at the point where the resistive strip 70 is nearest (i.e. where it is on the near side of the cylinder 60). The potential around angular direction, $\phi$, for fixed r and z, drops to a local minimum, indicated at 108, at the point above strip 62 where the resistive strip 70 is furthest away (i.e. where it is on the far side of the cylinder 60).

As the ions move in the axial direction following the axial field gradient away from the storage section 21 into the drift space 22 they approach the first potential barrier in the form of the first potential hump 102 in FIG. 3. This corresponds to approaching the helical resistive strip 70. This potential barrier also corresponds to the maximum 106 in the FIG. 4 plot. The ions cannot cross the barrier and instead follow the lowest potential path provided by the minimum 108 in FIG. 4 and so are driven in the arcuate direction, $\phi$. The combined axial and arcuate motion thus results in a helical motion of the ions around the inner electrode assembly 40 as the ions follow the potential barrier provided by the resistive strip 70. As the ions travel the helical path they become separated according to ion mobility. The helical motion thus substantially increases the path length of separation by ion mobility compared to the straight through path. The resistive strip 70 and hence the potential barrier provided by it terminates at the exit from the drift tube, so that the ions eventually reach the exit aperture 80 which has the switchable extraction voltage applied to it and is operable as described above. With the exit aperture 80 set to allow the ions to pass out of the drift tube 4 and through multipole 90, the ions separated according to their ion mobility can be passed to optional one or more further stages of processing and/or detection as described above. The exit aperture 80 can be operated with a switchable extraction voltage to gate ions only of desired ion mobility to the further stages.

The high resolution mode is preferably operated with a rotating arcuate electric field applied within the drift tube. In this case, this is achieved with the arcuate field electrodes or strips 33-35 operating as the ions move along the helical path through the drift tube. The conductive strips 33-35 are operated in this mode such that 5 to 50 volts are independently applied to them so that they provide a driving arcuate electric field (i.e. a field in the arcuate direction) to drive ions within the arcuate electric field in the arcuate direction, i.e. the same arcuate direction as they follow in the helical path. The driving arcuate electric field is preferably provided so that it spans a sector (i.e. in the arcuate direction) of less than 360 degrees, e.g. 240 degrees. This may be achieved by applying appropriate voltages to strips 33-35, e.g. with highest voltage on strip 33, lowest at 35 and intermediate at 34. Moreover, the driving arcuate field is preferably progressively applied in the arcuate direction (i.e. it moves in the arcuate direction by progressive application of voltages to the strips 33-35) so that the arcuate field rotates in the arcuate direction. The angular or rotational velocity (i.e. in the arcuate direction) of this rotating driving arcuate field is preferably synchronised with the angular or rotational velocity of ions of a selected ion mobility, K, so that such ions are moved through the drift tube along the helical path whereas ions of other ion mobility become out of phase with the progressive arcuate field and consequently may be slowed down or lost in the spectrometer, as described in more detail below. Thus, the ions of the selected ion mobility, K, will drift around the inner electrode assembly 40 (i.e. around wires 50) in the arcuate field, and always experience the optimum electric field E for driving the ions in the arcuate direction. For example, ions which are closer to the inner electrode assembly 40 and wires 50 experience a smaller arcuate field but, being located at a smaller radius r, they sustain substantially the same angular or rotational velocity as ions which are farther from the inner electrode assembly 40 and wires 50 but experience a larger arcuate field. Moreover, over the course of multiple radial oscillations, any difference in angular velocity between ions of the same mobility and similar m/z average out.

Figure 5:
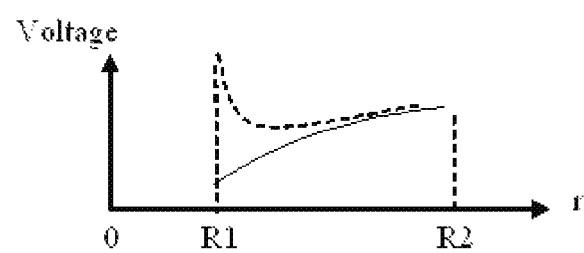
FIG. 5 shows potential profiles in the radial (r) direction for a sector in phase with an applied arcuate electric field in a high resolution filtering embodiment.
Figure 6:
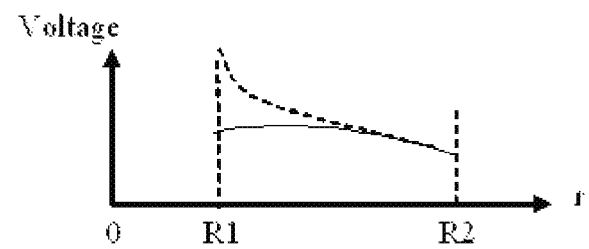
FIG. 6 shows potential profiles in the radial (r) direction for a sector out of phase with an applied arcuate electric field in a high resolution filtering embodiment.

The high resolution mode can be operated with ion filtering so that only ions of selected ion mobility are transmitted through the spectrometer with other ions being filtered out. In the high resolution filtering mode, when the driving arcuate electric field, as applied by the arcuate field electrodes, spans a sector of less than 360 degrees, e.g. so that it spans 240 degrees, the electric field in the remaining sector, e.g. the remaining 120 degrees, is preferably a defocusing field so that ions in this remaining sector become lost on the outer walls of the drift tube 4, i.e. on the outer cylinder 30. More preferably, the electric field in the remaining sector, e.g. the remaining 120 degrees, is preferably oriented in the opposite direction and/or voltages are applied to the strips 33-35 in such a way (e.g. the DC voltage on the strip in the remaining sector being lower than the DC voltage on the inner electrode assembly 40) that ions in this remaining sector experience a defocusing field (i.e. away from the inner electrode assembly 40) and become lost on the outer cylinder 30. The DC voltage on the strip in the remaining sector for example may be made lower than the collective DC voltage on the RF wires 50 and strips 62, 70 of the inner electrode assembly 40. FIGS. 5 and 6 show the total and the DC potential profiles along the radial direction r, at a fixed axial (z) position, for the sector where the driving arcuate field is present and the sector where the defocusing field is present respectively. In other words, the sector where the driving arcuate field is present is where the ions are in phase with the driving arcuate field and the sector where the defocusing field is present is where the ions are out of phase with the driving arcuate field. In the FIGS. 5 and 6, R1 represents the surface of the inner electrode assembly 40 and R2 represent the position of the outer cylinder 30. Referring to FIG. 5, describing where the driving arcuate field is present, it can be seen that the DC potential distribution (solid line) in the radial direction acts to confine the ions towards the inner electrode assembly 40 but the effect of the RF on the wires 50 is such that the total potential distribution (dotted line) prevents the ions from actually hitting the inner electrode assembly 40. Consequently, the ions are confined in a radial region between the outer cylinder 30 and inner electrode assembly 40. Referring to FIG. 6, describing where the defocusing field is present (i.e. where the driving arcuate field is not present), it can be seen that the DC potential distribution (solid line) and the total potential distribution (dotted line) in the radial direction act to pull the ions radially outwards towards the outer cylinder 30 so that the ions in this sector become lost on the outer cylinder.

The high resolution mode can alternatively be operated with trapping so that ions having such ion mobility that they are slower than the rotating arcuate electric field nevertheless remain trapped in the drift tube. This mode may be termed herein a rotating wave mode. The said ions may remain trapped in the drift tube, for example, until the rotational velocity of the arcuate field is changed to match the rotational velocity of trapped ions having a further selected ion mobility, e.g. after transmission through the drift tube of ions of the first selected ion mobility, and hence subsequently transmit the ions having that further selected ion mobility through the drift tube.

It should be noted that the embodiments above have ions of different m/z moving at different radii because quasi-potential of RF field is mass dependant while DC potential is not.

In order to improve the duty cycle of the instrument, injection into the ion mobility spectrometer could be performed at the same phase of every subsequent cycle of the arcuate field. In this case, trapping in the storage space 21 is not necessary and could be replaced simply by cycling the strength of axial field formed between the electrodes 31, 32 in the storage section between low and high settings to pulse the injection of ions into the drift space 22 of drift tube 4.

After the ions are extracted through the exit aperture 80, they may proceed to one or more further stages of ion processing (e.g. mass spectrometry, such as mass filtering or mass analysis, with or without ion fragmentation) and/or detection. In the example shown in FIG. 1, after the ions are extracted they are guided by ion guide 90 in the form of a multipole guide (preferably a quadrupole) that delivers the ions to a mass spectrometer downstream (not shown in FIG. 1). The ion mobility spectrometer according to the present invention may be utilised, for example, in various hybrid instrument configurations such as IMS/MS or IMS/MS/MS or IMS/(MS)$^n$, where IMS denotes a stage of ion mobility spectrometry and MS a stage of mass spectrometry. The stages of mass spectrometry may utilise any one or more mass spectrometer types such as: time-of-flight (TOF), ion trap (e.g. 3D ion trap or linear ion trap), magnetic sector, quadrupole, multipole and Fourier-transform mass spectrometer (FTMS) such as FT-ICR or an Orbitrap™ mass analyser. The IMS/MS/MS combinations are preferably any: IMS/Q/Trap or IMS/Q/Orbitrap™, where Trap denotes an ion trap, Q denotes a quadrupole mass filter and Orbitrap™ denotes an Orbitrap™ mass analyser. The ion mobility spectrometer according to the present invention is ideal for use with ion trap analysers, including an Orbitrap™ mass analyser.

Figure 7:
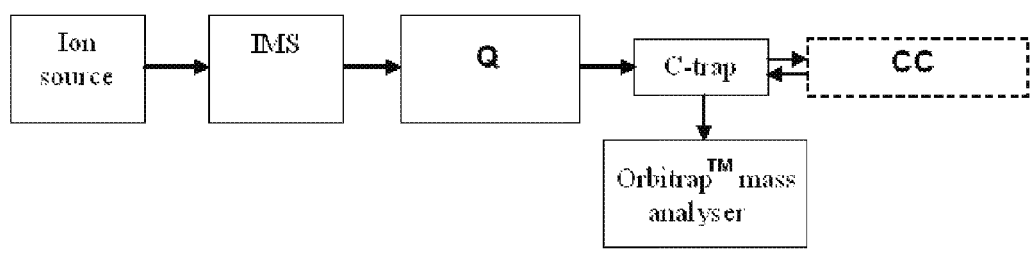
FIG. 7 shows schematically one embodiment of a hybrid IMS/MS/MS instrument including an ion mobility spectrometer according to the present invention.

FIG. 7 shows schematically a preferred embodiment of an IMS/MS/MS instrument wherein the IMS comprises the ion mobility spectrometer according to the present invention. The ion source is preferably a source such as an ESI source or MALDI source, especially for biological samples, including mixtures of proteins. The ions introduced from the source into the IMS are separated by the IMS as described herein, e.g. according to either the low resolution or high resolution modes and then are passed into the quadrupole mass filter (Q) which may be operated either as a mass filter or in RF—only mode wherein no mass filtering is performed. From the quadrupole mass filter, the ions can be passed into a high resolution mass spectrometer, in this example an Orbitrap™ mass analyser. In a known step, the ions are first passed from the quadrupole into a curved linear trap (C-trap) for pulsed injection into the Orbitrap™ mass analyser. Optionally, ions may be sent from the C-trap to a collision cell (CC) for fragmentation and the fragmented ions may be sent back to the C-trap for injection to the Orbitrap™ mass analyser.

Alternatively, the ions exiting from the ion mobility spectrometer may be detected by an ion detector positioned after the exit aperture from the ion mobility spectrometer, i.e. without further processing.

In one type of operation mode, a mass spectrometer may be arranged to detect ions extracted from the IMS of selected mobility having one or a limited number of m/z values so that the instrument thereby provides an ion specific detector. In a more typical mode of operation, a mass spectrum is obtained by a mass spectrometer for each narrow range of ion mobilities transmitted by the IMS (i.e. for each ion mobility peak). For this latter mode, preferably the extraction of the ions from the IMS is pulsed, preferably with a delay between pulse corresponding to the drift time between ion mobility peaks. The pulses of extracted ions are then each mass analysed to provide the mass spectrum, thereby potentially resolving a single ion mobility peak into its m/z components.

Figure 8:
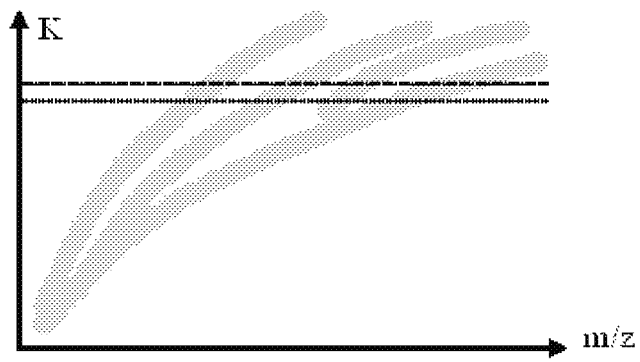
FIG. 8 shows a two-dimensional (2D) mobility/mass diagram which can be obtained using an embodiment of the present invention.

In a preferred mode of operation, the ion mobility spectrometer 2 is operated in the high resolution filtering mode described above so that it transmits ions of only a narrow range of ion mobilities, K, albeit with a high duty cycle. Referring to FIG. 8 this narrow range of ion mobilities K (i.e. between the dotted lines in the Figure) is shown on a mobility/mass plot of K against m/z. A subsequent mass analyser, such as an ion trap, receives the ions in the narrow range of ion mobilities and performs a mass analysis, i.e. an m/z scan. For example, using the hybrid instrument shown in FIG. 7 the quadrupole mass filter (Q) can be operated in RF-only mode so as not to provide mass filtering and then ions in the narrow range of mobility are stored in the C-trap and ejected into the Orbitrap™ mass analyser for the mass analysis to be performed. Subsequent scans by the ion mobility spectrometer to transmit further ranges of ion mobilities, K, are then performed and mass analysis is performed for each mobility scan so that a two-dimensional (2D) mobility/mass diagram can be obtained as shown in FIG. 8. Regions of the mobility/mass plot where ion species are detected are shown in the Figure by the shaded bands. Using the known correlation between K and m/z as shown in FIG. 8, analysis speed could be increased by combining several values of K into one mass spectrum, e.g. by accumulating ions of several values of K in the C-trap before analysing them together in the Orbitrap™ mass analyser. In addition, as described above, fragmentation in a collision cell could be used to create fragments of selected ions.

Figure 9:
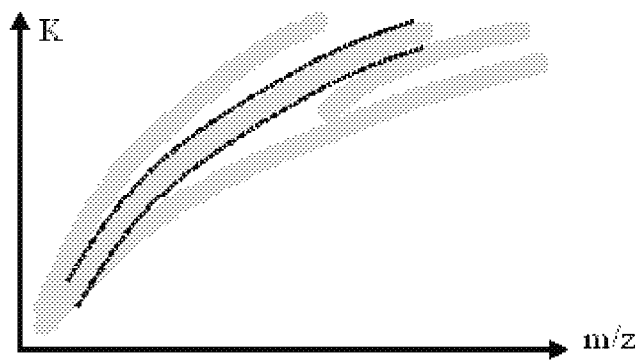
FIG. 9 shows a linked-scan method which can be performed using an embodiment of the present invention whereby ions of a set mobility/mass ratio are scanned.

Another preferred method is illustrated with reference to FIG. 9. In this so-called linked-scan method, it allows selection only of ions of certain type(s), e.g. of selected charge states, which can greatly improve the dynamic range of analysis of complex mixtures and avoid analysing analytically useless ions (e.g. singly-charged and polymers ions in the case of peptide mixtures). In this linked-scan method, a mass filter, such as the quadrupole mass filter in FIG. 7 for example, is rapidly scanned simultaneously with the mobility scanning by the IMS so that only ions of defined mobility/mass ratio or lying on a defined curve on a mobility/mass diagram are passed into a subsequent mass analyser, such as the Orbitrap™ analyser of FIG. 7 for example. Prior to the latter mass analysis stage, the ions selected by the defined mobility/mass ratio are preferably accumulated, most preferably in an ion trap, e.g. such as the C-trap in FIG. 7. The accumulated ions can then be released from the ion trap into the mass analyser. In FIG. 9, a representative mobility/mass ratio accumulated in the ion trap in one scan is shown between the dotted lines. As mentioned, at the end of the scan, all of the accumulated ions can be mass analysed, e.g. injected into the Orbitrap™ analyser and the mass spectrum acquired. In such an operation, a high-resolution mass spectrum, such as obtained using an Orbitrap™ analyser, can be obtained which will include only ions of interest (e.g. 2- or 3-charged ions, or glycopeptides only, etc.) and therefore the space charge capacity of the trap is utilised to the full. In a similar manner, one or more subsequent scans can be taken at different mobility/mass ratios. The mass resolution of the mass filter could be chosen to be similar to that of the IMS so that overall duty cycle remains respectable (e.g. 1-2%). To match the repetition rate of the Orbitrap analyser, the whole scan should take 50 to 1000 ms depending on required resolutions in IMS and quadrupole. In addition, certain selected m/z could be fragmented in the optional collision cell to provide fragments for confirmation of a corresponding precursor ion.

Other instrument configurations than the configuration shown in FIG. 7 can be envisaged of course, e.g. a Q-IMS-TOF configuration, especially such a configuration including a cell for fragmentation of ions of the same m/z but different mobility. Instead of quadrupole, other types of fast mass selectors could be used, for example based on resonant separation on time-of-flight as described in the applicant's co-pending applications GB 1020038.4 and GB 1020039.2.

It will be appreciated in view of the principle of operation of the present invention that the spectrometer could be constructed the opposite way around to the particular preferred embodiment shown, i.e. instead with the helical electrode 70 located at the inner surface of the outer electrode 30 and RF electrodes 50 radially inwards of but close to the inner surface of that outer electrode. The arcuate field electrodes 33-35 could be placed at the surface of the inner electrode assembly 40 in such a case. In such embodiments, the direction of the DC field in the radial direction needs to be reversed to that described.

FIG. 11 describes another embodiment of the present invention which provides DC-only separation of ions. In this embodiment, the arcuate field electrodes 33-35 are replaced by a helical potential well provided by inner and outer helical electrodes as hereafter described. In this case, both inner and outer cylinders 30 and 40 contain the double-helix arrangement of resistive strips 62, 70 on dielectric cylinders, with DC potential distributions formed along the helices when appropriate voltages are applied to the strips. The outer cylinder 30 in this case comprises a dielectric material which has the strips 62', 70' arranged on its inner surface, facing the inner cylinder 40. The inner cylinder 40 in this case has the strips 62, 70 formed in its outer surface, facing the outer cylinder 30. The inner cylinder 30 is hollow as shown, although this need not be the case as explained below. As in the above embodiments, one of the helix strips 62, 70 (62', 70') in each cylinder has its applied voltage elevated relatively to the other strip so that ions can move only along the potential valley formed. To provide RF trapping, an RF voltage is coupled to the inner resistive strips 62, 70 from a metal RF electrode 200 via distributed capacitance of several hundreds of pF formed in the small gap (few mm) between the RF electrode and resistive strips 62, 70. The RF electrode 200 could be embedded into the dielectric of inner cylinder 40 or vacuum-isolated from it (as shown) and has RF voltage of 200 to 2000 V amplitude and 3 to 6 MHz frequency applied to it. Radial trapping could be performed either by biasing the outer strips 62', 70' relatively to the corresponding inner strips 62, 70 (so that mass-dependent effective potential of FIG. 5 is formed) or by coupling similar RF into the outer electrodes, 62', 70' as well. Gap between strips 62 and 70, especially on the inner cylinder should be minimised to reduce penetration of DC voltage from the RF electrode into the ion mobility separation (IMS) region (drift space). As an example of construction, a thin tube of lead silicate glass could be hydrogen reduced to get a thin conductive film on the outside and then laser ablation could be used to cut a spiral groove through this layer thus forming double helix with very high or infinite resistivity between windings. Alternatively, metal RF electrode could be coated with isolating plastic (e.g. PTFE or polycarbonate), then a shroud of conductive plastic press-fitted on it and then cut through (but only partially through isolating plastic) by laser to form helical strips. Outer strips 62', 70' could have a larger separation as there is no need to shield RF instead, this would allow for DC field from outer resistive coating 240 to penetrate into the IMS volume for purposes described below.

As the radial voltage difference should be kept constant along the entire length of the device, it means that the arcuate field would be inversely proportional to radius. Therefore the relative variation of the field over the size of the ion beam should be minimised, either by reducing beam size by better focusing or decreasing variation by using bigger radius (the latter reducing quasi-potential of RF field). For the drift tube dimensions given above (50 mm outer diameter of the inner cylinder and 60 mm inner diameter of the outer cylinder), IMS resolving powers in excess of 100 to 200 are feasible. To avoid electrical breakdown due to a substantial voltage difference between the ends of the gas-filled IMS tube which could reach hundreds or, when higher resolving powers are desired, even thousands of Volts, IMS should be always operated below the breakdown threshold determined by Paschen curve, preferably above $10^{-2}$ mbar*m. Fortunately, extremes of voltage are met at the opposite ends of the IMS tube, so the characteristic size of L could be used (200 mm in our case). Then at 2 mbar pressure the maximum voltage should stay below 2000 V for nitrogen and 600 V for helium which is already feasible for high resolving powers according to eq. 2. It is also important to observe that RF voltages across the gap also stayed below the Paschen curve, preferably below few hundred volts.

In operation, ions from injection multipole 10 are trapped in the RF-only storage device 230, then the voltage offset of this storage device is lifted above the elevated voltage on the front of IMS tube and ions are thereby injected into the IMS tube by reducing the voltage on the gate aperture 260. Such "energy lift" allows both ion source and subsequent mass analysers to be kept at lower voltage offsets relatively to ground.

In high-resolution mode, voltages between strips 62 and 70 on the inner cylinder 40 and between their counter-parts 62' and 70' on the outer cylinder are sustained according to FIG. 3 in such a way that axial electric fields force ions from neighbouring windings of strip 70 towards strip 62. Ions find themselves in a helical potential trough which forces them to follow the electric field lines along the helical path between inner and outer cylinders. Effective path lengths of up to several meters over voltage drop of few kV is achievable in this mode.

In low-resolution mode, voltage offset of strip 70 is reduced so that no barrier exists but rather a linear axial voltage distribution is formed between it and strip 62, thus forcing ions straight along the drift tube of the IMS. Additional axial field is created by applying voltage along the outer coating 240. An arcuate electric field still forces ions to rotate around the axis of the inner cylinder, but this time the step of the helix is considerably longer and the travel time shorter. By shaping appropriately the outer coating 240 and supplying sufficiently high voltages, arcuate field inside IMS could be reduced to zero so that ions travel essentially straight from entrance to exit.

In transmission mode, operation is similar to low resolution but this time RF-storage 230 is cycled with highest possible frequency between filling and releasing ion packets (e.g. 200-500 times per second) so that high ion flows up to $10^9$-$10^{10}$ ions per second can be transmitted. This requires pressure in RF-storage to exceed $10^{-2}$ mbar. Alternatively, DC voltage along the strips 62, 70 could be reduced to few tens of volts and there will be no need for such "energy lift" in the ion storage: i.e. ion flow could pass through continuously.

It will be appreciated that the ion mobility spectrometer of the present invention could be used also for field-asymmetric IMS (FAIMS). Accordingly, the ion mobility spectrometer of the present invention may comprise a field-asymmetric ion mobility spectrometer. For this use, it is sufficient to increase the electric field/pressure ratio, E/P, significantly above 200 V/(m*mbar), preferably above 1000 V/(m*mbar). Alternatively, RF on wires could be made asymmetric which then result in additional net displacement of ions in the field. This in turn moves ions from their optimum position to another radius where they obtain different drift speed, run out of phase with the rotating arcuate electric field and get lost on the inner or outer electrodes.

Data dependent acquisition could be employed using the present invention to choose between different modes of operation (e.g. those presented above and others) depending on results coming in real time from a mass spectrometric detector. For example, an overview broad mass range spectrum could be used to select m/z of interest for IMS analysis and fragmentation so that MS/MS spectra of selected isomers could be acquired.

Advantages of the invention include the ability to switch between different modes of operation, e.g. from rapid transmission mode (ion guiding) or low transmission IMS mode to various high-resolution IMS modes such as a high-resolution linked-scan IMS-MS mode. The invention enables high-resolution ion mobility filtering in a rotating field. The invention enables a helical path thus saving space for a high-resolution ion mobility separation device but within a straight drift tube thus providing a simple construction.

It will be appreciated that the current invention could be also operated in multiplexed mode when more than 1 ion packet is injected during the mobility separation. Hadamard and pseudo-random encoding could be employed with appropriate deconvolution of resulting data.

The term straight used herein means generally or substantially straight, not necessarily strictly geometrically or mathematically straight and the term helical used herein means generally or substantially helical, not necessarily strictly geometrically or mathematically helical. It will be appreciated, for example, that it is not essential that elements of the present invention be strictly geometrically or mathematically straight or strictly geometrically or mathematically helical, as the case may be, in order for the invention to work.

As used herein, including in the claims, unless the context indicates otherwise, singular forms of the terms herein are to be construed as including the plural form and vice versa. For instance, unless the context indicates otherwise, a singular reference herein including in the claims, such as "a" or "an" means "one or more".

Throughout the description and claims of this specification, the words "comprise", "including", "having" and "contain" and variations of the words, for example "comprising" and "comprises" etc, mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example" and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention claimed is:

1. An ion mobility spectrometer for separating ions according to their ion mobility comprising a drift tube having therein a drift space and in the drift space at least two ion separation paths of different lengths, wherein the at least two ion separation paths comprise a first ion separation path which is straight and a second ion separation path which is helical.

2. An ion mobility spectrometer as claimed in claim 1 wherein the drift tube is straight in an axial direction.

3. An ion mobility spectrometer as claimed in claim 1 wherein the drift tube comprises an axially extending outer electrode assembly and an axially extending inner electrode assembly wherein the outer electrode assembly annularly surrounds the inner electrode assembly and the drift space is an annular drift space defined between the outer electrode and the inner electrode assembly.

4. An ion mobility spectrometer as claimed in claim 1 wherein ions are radially confined in the drift tube in use by applying an RF field in the drift tube by means of axially extending RF electrodes spaced annularly around the axis of the drift tube.

5. An ion mobility spectrometer as claimed in claim 4 wherein the ions are further radially confined by applying a radial DC field and the RF electrodes are spaced annularly around an inner electrode assembly such that the ion separation paths are located radially outwards of the RF electrodes.

6. An ion mobility spectrometer as claimed in claim 3 wherein ions are radially confined in the drift tube in use by applying a radial DC field in combination with an RF field in the drift tube applied by means of one or more RF electrodes coupled to the inner electrode assembly and/or outer electrode assembly.

7. An on mobility spectrometer as claimed in claim 1 comprising an axial driving electrode for applying an axial electric field in the drift space to drive the ions axially in the drift tube.

8. An on mobility spectrometer as claimed in claim 1 comprising at least one guiding electrode for applying a switchable voltage thereto for providing a guiding potential barrier to direct the ions along the helical separation path.

9. An ion mobility spectrometer as claimed in claim 8 wherein the at least one guiding electrode comprises a helical guiding electrode.

10. An ion mobility spectrometer as claimed in claim 8 wherein the at least one guiding electrode is part of the inner electrode assembly and/or outer electrode assembly.

11. An ion mobility spectrometer as claimed in claim 9 comprising at least one helical axial driving electrode and the helical guiding electrode and helical axial driving electrode are arranged to form a double helix.

12. An ion mobility spectrometer as claimed in claim 1 comprising arcuate field electrodes arcuately spaced around the axis of the drift tube to provide a rotating arcuate electric field wherein the rotational velocity of the rotating arcuate field is synchronised with the rotational velocity of ions of selected ion mobility.

13. An ion mobility spectrometer as claimed in claim 12 wherein the rotating arcuate electric field spans a sector of less than 360 degrees and the electric field in the remaining sector is a defocusing field so that in use ions in the remaining sector become lost on a wall of the drift tube.

14. An ion mobility spectrometer as claimed in claim 12 wherein the duty cycle of the ion mobility spectrometer is increased in use by injecting ions into the ion mobility spectrometer at the same phase of subsequent cycles of the rotating arcuate field.

15. An on mobility spectrometer as claimed in claim 1 comprising a pulsed on injector for the release of ions into the drift tube.

16. An ion mobility spectrometer as claimed in claim 1 comprising a gate electrode for extraction of the separated ions from the drift tube.

17. An on mobility spectrometer as claimed in claim 1 which is coupled to a mass filter positioned downstream of the ion mobility spectrometer which in use is scanned simultaneously with on mobility scanning by the ion mobility spectrometer so that only ions of pre-determined mobility/mass ratio or lying on a pre-determined curve on a mobility/mass diagram are selected for subsequent processing or detection.

18. An ion mobility spectrometer as claimed in claim 17 wherein the selected ions are accumulated together in an ion trap before mass analysis of the accumulated ions.

19. A method of separating ions according to their on mobility comprising:
providing a drift tube having therein a drift space and in the drift space at least two ion separation paths of different lengths;
selecting one of the on separation paths for ions to follow; and
causing ions to follow the selected on separation path and separating the ions along the selected ion separation path according to their ion mobility, wherein one of the separation paths is helical and the ions are guided on the helical path by a helical potential barrier and the ions are radially confined in the drift tube in use by applying an RF field in the drift tube in combination with radial DC field.

20. An ion mobility spectrometer for separating ions according to their ion mobility, having electric field generation means being switchable between conditions to provide in a first condition a separating electric field substantially aligned with a first separation path of a first length and in a second condition a different separating electric field substantially aligned with a second separation path of a second length different to the first length.

21. An on mobility spectrometer as claimed in claim 20 wherein the first path is straight and the second path is curved.

22. An on mobility spectrometer as claimed in claim 21 wherein the curved path is a substantially helical path.

23. An ion mobility spectrometer as claimed in claim 21 comprising at least one guiding electrode for applying a switchable voltage thereto for providing a guiding potential barrier to direct the ions along the curved separation path.

24. An ion mobility spectrometer as claimed in claim 1, wherein the second ion separation path surrounds an axially extending inner electrode assembly.

* * * * *